United States Patent [19]
Casey

[11] Patent Number: 5,842,856
[45] Date of Patent: Dec. 1, 1998

[54] RELEASE SYSTEM FOR TREATMENT OF A BROKEN JAW

[76] Inventor: Kevin M. Casey, 5028 NW. Woodridge Dr., Parkville, Mo. 64151

[21] Appl. No.: 596,541

[22] Filed: Feb. 5, 1996

Related U.S. Application Data

[63] Continuation of Ser. No. 274,010, Jul. 12, 1994, abandoned.
[51] Int. Cl.⁶ .................................................... A61C 7/26
[52] U.S. Cl. ................................. 433/19; 433/20; 433/22
[58] Field of Search ................................. 433/10, 17–20, 433/22, 215; 602/5, 17, 902; 606/57

[56] References Cited

U.S. PATENT DOCUMENTS

| | | | |
|---|---|---|---|
| 1,638,006 | 8/1927 | Aderer | 602/5 |
| 1,797,481 | 3/1931 | Preston | 602/5 |
| 2,481,177 | 9/1949 | Tofflemire | 602/5 |
| 2,502,902 | 4/1950 | Tofflemire | 606/54 |
| 3,593,421 | 7/1971 | Brader | 433/22 |
| 4,202,328 | 5/1980 | Sukkarie | 433/18 |
| 4,230,104 | 10/1980 | Richter | 433/18 |
| 4,311,463 | 1/1982 | Glattly | 433/18 |
| 4,872,449 | 10/1989 | Beeuwkes, III | 433/19 |
| 5,035,614 | 7/1991 | Greenfield | 433/20 |
| 5,087,202 | 2/1992 | Krenkel | 433/215 |

OTHER PUBLICATIONS

"Use of Cotter Key in Intermaxillary Ligation of Fractures Allowing Quick Release in Case of Nausea and Vomitting", Hamilton D. Harper, Presented at 23rd Annual Mtg. of S. W. Society of Orthodontists, Tulsa, Oklahoma, Mar. 1943.

"Rip Cord for Emergency Release of Immobilized Mandible", Kimble A. Traeger, U.S. Armed Forces Medical Journal, pp. 329–335, vol. VI, No. 3, Mar. 1995.

*Primary Examiner*—Stephen R. Funk
*Attorney, Agent, or Firm*—Shook, Hardy & Bacon, L.L.P.

[57] ABSTRACT

A release system for treatment of a broken jaw comprises an upper and lower arch bar conformable to the curvature of the dental arches. The upper arch bar presents a series of interaligned loops which presents a channel for supporting a release bar extending therethrough. Upon wiring the arch bars to the respective dental arches, the lower arch bar is wired to the release bar so as to immobilize the dental arches and associated jaw. Upon imminent vomiting the user removes the release bar from its channel so as to disengage the release bar wiring from the associated upper arch bar. The loop channel supports the release bar so as to prevent kinking and bending of the release bar during wiring and wear. Various arch bars with releasable loops attached thereto are disclosed. Hanger elements for use with individual teeth are also disclosed which define courses for the release bar in lieu of the use of the loop channel on an arch bar. Caps cover the twisted ends of ligature wires to preclude oral abrasion.

10 Claims, 3 Drawing Sheets

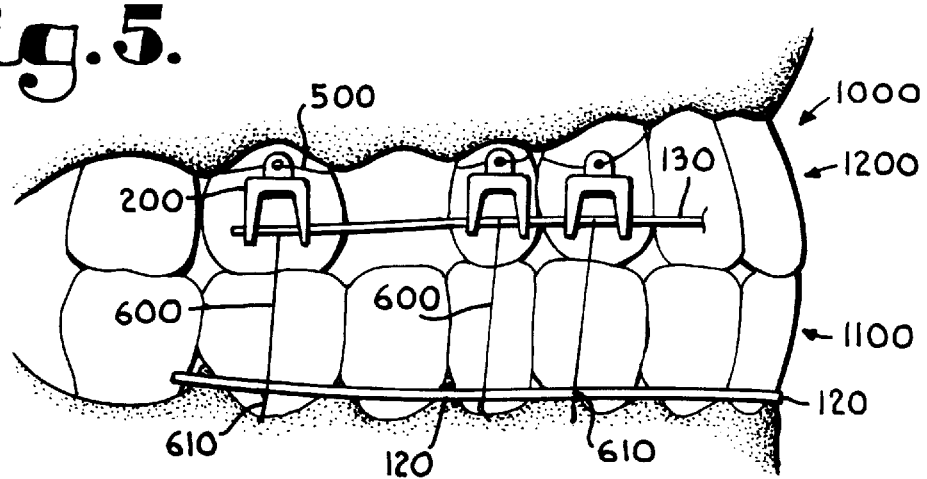
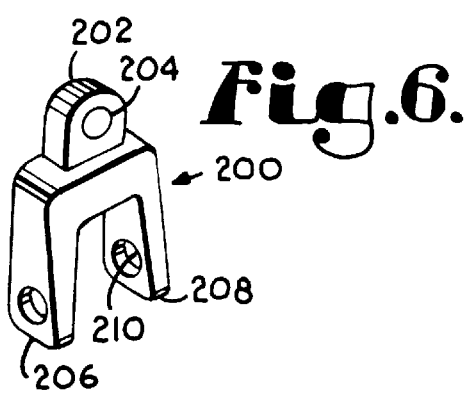
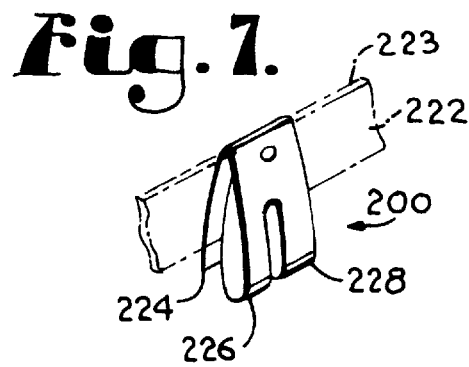
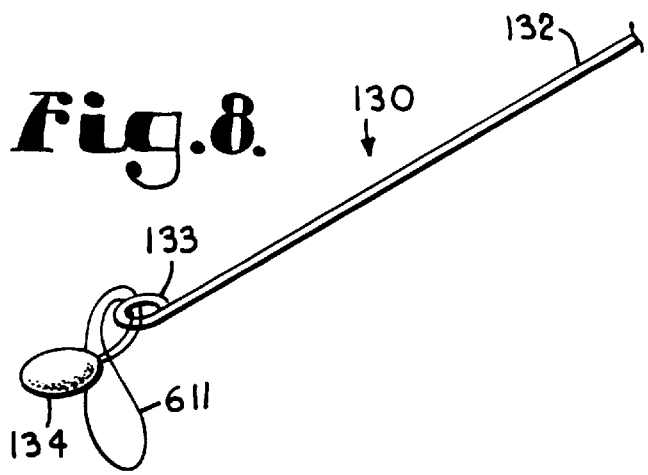
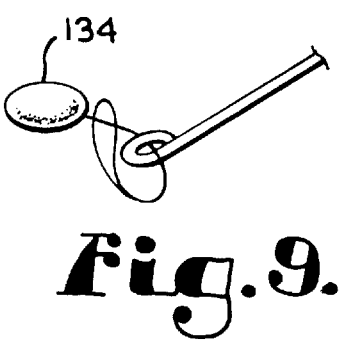

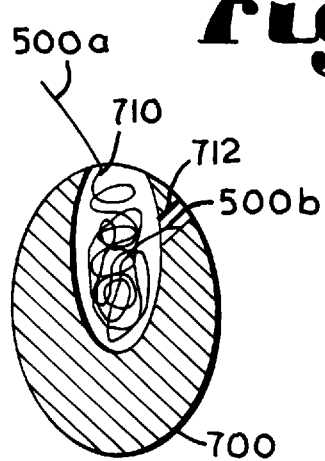
Fig.10.
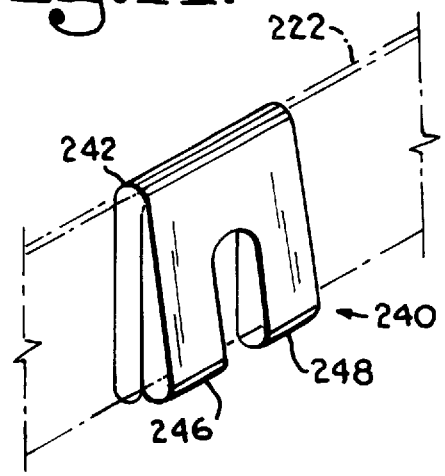
Fig.11.
Fig.12.
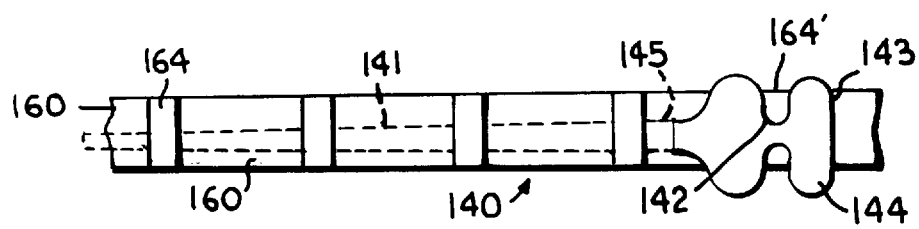
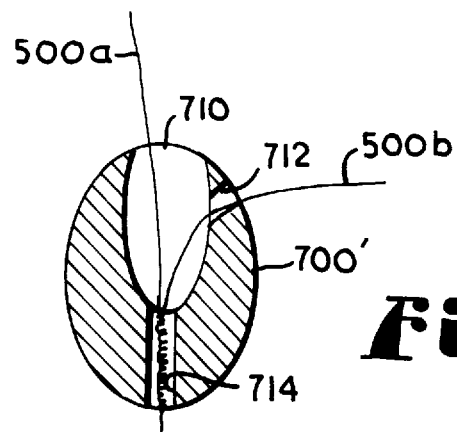
Fig.13.

RELEASE SYSTEM FOR TREATMENT OF A BROKEN JAW

This application is a continuation of Ser. No. 08/274,010, filed Jul. 12, 1994, now abandoned.

BACKGROUND OF THE INVENTION

1. Field of the Invention

This invention relates to an intermaxillary fracture splint/orthodontic appliance for treatment of a broken jaw, and more particularly, to an improved orthodontic appliance allowing for a quick, unobstructed release of the ligatures which immobilize the broken jaw.

2. Discussion of the Prior Art

The basic principle of intermaxillary ligation comprises the wiring of the upper and lower dental arches together so as to immobilize the jaw allowing for the fracture to heal.

Various means of ligation have been utilized including the use of elastic materials, such as rubber bands, extending between upper and lower arch bars wired to the teeth. Also, wires extending between upper and lower arch bars, as wired to the teeth, have been used. The arch bars present tabs about which the wires or elastics are wound.

One problem with past appliances is that the tightly wired patient may become ill causing vomiting. As the dental arches are tightly wired one to the other, the patient may not be able to quickly sever the ligatures so as to open his/her mouth to spew the vomit. Accordingly, the patient may suffocate.

A cotter key arrangement has been proposed which extends an elongated bar through wire loops individually wound about teeth of a dental arch. The loops are spaced along the upper and lower dental arches. Wiring extends from one dental arch and about the cotter key so that the jaw is clamped shut. Upon pulling the cotter key from the loops the patient's jaw is said to be free to open so as to expel the vomit.

One problem is that the formation of the wire loops is time consuming and the effectiveness of the wiring is subject to the skill of the treating physician. Moreover, during wiring and/or wear the cotter key may snag or hang on the wire loops, ligatures or elastics wound therearound. Also the plurality of wire loops extending from the teeth may become displaced from their original position. As these wire loops are not properly aligned the cotter key may have difficulty in being drawn therefrom.

OBJECTS AND SUMMARY OF THE INVENTION

In response thereto I have invented a quick release system which comprises an arch bar having a plurality of fixed, preferably closed, loops extending therefrom. The loops define a channel for supporting a release bar extending therethrough. The arch bars and release bar are first conformed to the dental arch and then attached thereto. An intermaxillary tie wire extends from an arch bar on the opposed dental arch and is then wound about the release bar. Upon tightening of the tie wire the arch bars are drawn together so that the jaw is immobilized. The loop channel offers support to the release bar so as to preclude any bending or kinking of the release bar during wiring. Moreover, during use the closed loops hinder formation of oral debris about the release bar/loop interface. The loops are aligned along the arch bar and remain aligned during use. Upon imminent vomiting the release bar is pulled from the loop channel. Thus, the intermaxillary tie wire is no longer linked to the arch bar which allows the dental arches to separate. The loop alignment, the support of the release bar by the loop channel and the oral debris inhibition cooperate to hinder an undesirable bending, kinking and/or snagging of the release bar which could hinder its withdrawal. I also provide various alternative loop elements for attachment to an arch bar and hangers having loops thereon for attachment to an individual tooth so as to present alternative loop channels for the release bar. Protectors for enclosing the twisted ends of ligature wires and the release bar are also provided.

It is therefore a general object of this invention to provide an orthodontic appliance for use in the treatment of jaw fractures.

Another general object of the invention is to provide an orthodontic appliance, as aforesaid, which allows the user to quickly release the binding effect on the jaw so as to allow for jaw mobilization.

A further object of this invention is to provide an orthodontic appliance, as aforesaid, which will effectively operate during the release mode.

Still another object of this invention is to provide an orthodontic appliance, as aforesaid, which diminishes the probability of kinking and/or bending of the appliance components during use.

A still further object of this invention is to provide an orthodontic appliance, as aforesaid, which diminishes the interference of oral debris with the appliance during use.

Still another object of this invention is to provide an orthodontic appliance, as aforesaid, which does not abrade the surrounding oral tissue.

Still another object of this invention is to provide an orthodontic appliance, as aforesaid, which presents a channel for supporting a release bar during use.

A further object of this invention is to provide an orthodontic appliance with channel, as aforesaid, presented by a series of loops projecting from an arch bar.

Another particular object of this invention is to provide an orthodontic appliance with a channel, as aforesaid, presented by loops selectably mounted along the arch bar.

Another particular object of this invention is to provide an orthodontic appliance with support a channel, as aforesaid, presented by loops associated with individual teeth of a dental arch.

Other objects and advantages of this invention will become apparent from the following description taken in connection with the accompanying drawings, wherein is set forth by way of illustration and example, embodiments of this invention.

BRIEF DESCRIPTION OF THE DRAWINGS

FIG. 5 is a side view of the upper and lower dental arches showing an alternative embodiment of the release system;

FIG. 6 is a perspective view of a hanger forming a part of the release system of FIG. 5 on an enlarged scale;

FIG. 7 is an alternative embodiment of a hanger as mounted on an arch bar;

FIG. 8 is a perspective view of the release bar, on an enlarged scale, showing a grip being tied in place at the user operable end thereof;

FIG. 9 is another view of the proximal end of the release bar of FIG. 8;

FIG. 10 is a central section view, on an enlarged scale, of a cap for covering the ends of ligature wires;

FIG. 11 is an alternative embodiment of a hanger element attached to an arch bar on an enlarged scale;

FIG. 12 illustrates a holder for a release bar in place on an arch bar.

FIG. 13 is a central section view, on an enlarged scale, of an alternative cap for covering the ends of ligature wires.

DETAILED DESCRIPTION OF THE PREFERRED EMBODIMENT

Figure 1:
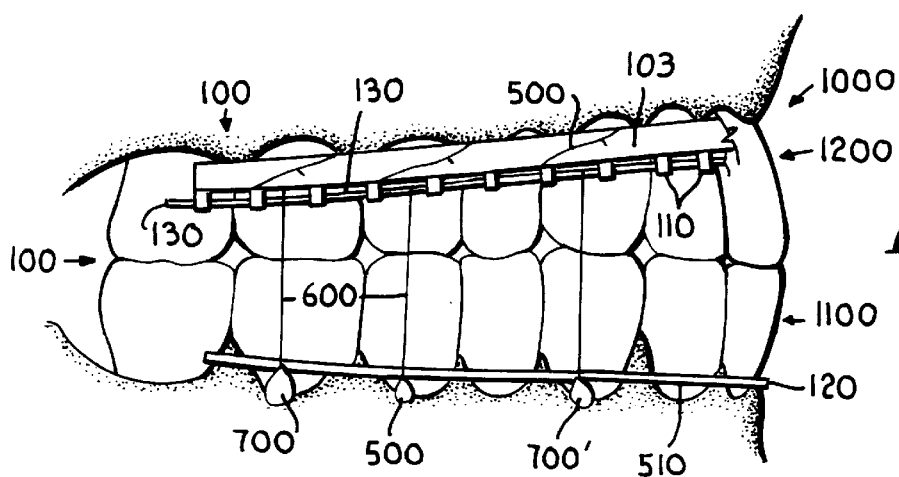
FIG. 1 is a side view of the upper and lower dental arches showing the release system in place.

Turning more particularly to the drawings FIG. 1 shows the right side of a patient's jaw 1000 as comprising a maxillary or upper dental arch 1200 and a lower/mandibular dental arch 1100. As shown, both dental arches contain all the teeth therein. It is understood that the left side of the jaw 1000 is a reverse, mirror image thereof. Thus, the below-described description of embodiments may also be utilized on the opposite left side of the jaw.

Figure 2:
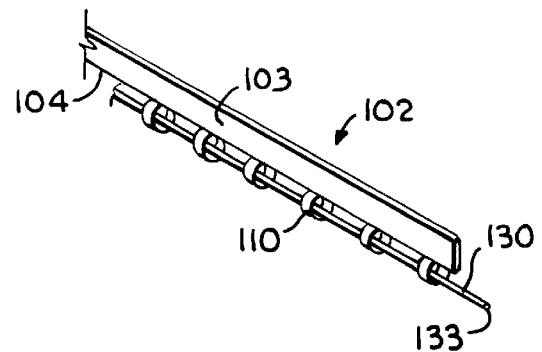
FIG. 2 is a perspective view showing a portion of the arch bar of the device of FIG. 1 with the release bar passing through a support channel.

FIG. 1 shows a first embodiment of the quick release system 100 in place on the lower 1100 and upper 1200 dental arches. The system 100 includes an upper arch bar 102 (FIG. 2) and lower arch bar 120. The lower arch bar 120 generally comprises a cylindrical shaft made of a malleable material conformable to the curvature of the lower dental arch 1100. The upper arch bar 102 generally comprises a flat band 103 of a malleable material which is conformable to the curvature of the upper 1200 dental arch.

Depending from the lower longitudinal edge 104 of band 103 is a plurality of longitudinally spaced, circular loops 110. The closed loops 110 present interaligned apertures along the longitudinal extent of the arch bar 102. The loops 110 present a longitudinally extending channel generally parallel to the longitudinally extending band 103 of the arch bar 102. Alternately, the lower arch bar 120 could be provided with the plurality of loops.

In use the lower arch bar 120 is conformed to the curvature of the lower dental arch 1100. This bar 120 is tied to the lower dental arch 1100 by ligature wires 500 wound about and between the teeth and the arch bar 120. The ligature wires 500 are twisted 510 so as to selectably vary the bearing relationship of the bar against the adjacent teeth line 1100. Wax or caps 700, as below described, surround the twists 510 to diminish abrasion of the adjacent oral tissue. In a similar manner the upper arch bar 102 is conformed to the curvature of the upper/maxillary dental arch 1200. This bar 102 is similarly fastened by ligature wires 500 wound about and between the teeth and arch bar 102. Ligature wires may also be coupled between the arch bar 102, loops 110 and facial bones, if required. Accordingly, the upper 102 and lower 120 arch bars are secured to their respective dental arches 1200, 1100.

The release bar 130 comprising a shaft 132 and handle 133 is preferably inserted through the loop 110 channel of arch bar 102 during arch bar 102 conformation. Thus, the curvature of release bar 130 is similar to the curvature of arch bar 102 and the adjacent teeth line 1200. The bar 130 is then removed from loop 110 channel to allow the arch bar 102 to be secured to the dental arch 1200 as above described. Upon securement the shaft 132 of release bar 130 is inserted through the loop 110 channel with the loops 110 offering support to the shaft 132 of release bar 130. Caps may be placed at the distal end of shaft 132 to preclude oral abrasion. As such the release bar 130 presents an arch bar that is displaced from the arch bar 102 and in a generally parallel relationship thereto. This bar 130 presents a support for subsequent intermaxillary wiring 600.

Once the arch bar 102 and release bar 130 are in place one end of a plurality of tie wires 600 is then wound about the upper release bar 130 and the lower arch bar 120. This configuration is repeated along the extent of the teeth lines 1100, 1200. The winding of the tie wires 600 draws the arch bars 102, 120 one towards the other. Upon completion, the dental arches 1100, 1200 are relatively immobile. Accordingly, the jaw is likewise immobile so as to allow the jaw fracture to heal.

It is also understood that elastics may extend between the upper 102 and lower arch bars. If elastics are used the release bar 130 is sequentially inserted through the loops 110 and through the upper end of the elastics. The lower end of the elastics is then attached to a lower arch bar.

During wear, if patient vomiting is imminent, the handle 133 or grip 134 thereon of release bar 130 is grasped and withdrawn from its position extending through the loop 110 channel. As the loop 110 channel has supported the release bar 130 during winding of the tie wire, no kinks or bends in the release bar 130 are likely to occur. Moreover, the loops 110 of the channel have remained interaligned during tying and wear. Thus, the maintenance of the loop 110 alignment and conforming curvature of the release bar 130 diminishes the possibility of the release bar 130 snagging on the loops 110 during this withdrawal action.

The closed loops 110 having no free edges not only diminish abrasion of the adjacent oral tissue but also preclude the formation of oral debris in the bar 130/loop 110 interface. This debris preclusion further enhances the sliding movement of the bar 130 from the loop 110 channel during the withdrawal mode. Upon release the respective arch bars 102, 120 and dental arches 1100, 1200 can now move in opposed directions allowing the mouth to open and expel the vomit.

Figure 4:
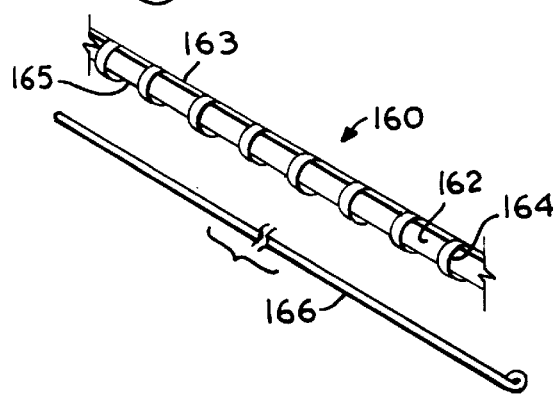
FIG. 4 is a perspective view showing a portion of the alternative arch bar of the release system of FIG. 3 with the release bar removed from the support channel.
Figure 3:
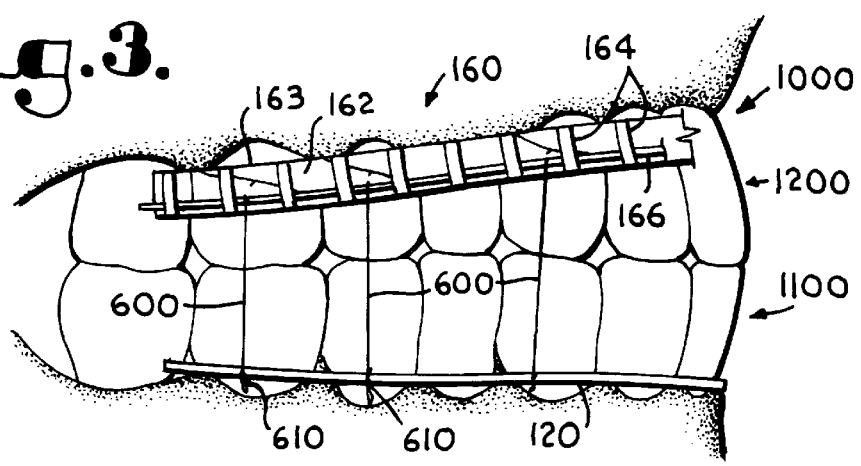
FIG. 3 is a side view of the upper and lower dental arches showing an alternative embodiment of the release system.

FIGS. 3 and 4 show the use of another embodiment of an arch bar 160 as comprising a metal band 162 with a plurality of semi-circular loops 164 extending between the upper 163 and lower 165 edges. A release bar 166 extends through the loops 164. This FIG. 4 bar 160 may be utilized in the system 100 in lieu of arch bar 102 as above described.

FIGS. 5 and 6 show the use of a plurality of hangers 200 (FIG. 6) which are tied to the teeth by the ligature wires 500. Such hangers 200 are used with the quick release bar 130 in lieu of the arch bar 102 particularly when the patient is missing teeth along the dental arch 1200. Each hanger 200 generally comprises a tab 202 presenting an aperture 204 for passage of the ligature wire 500 therethrough. Depending from the eyelet 202 are a pair of first 206 and second 208 support legs having apertures 210 therein. Upon placement of a plurality of the hangers 200 along the dental arch 1200 the apertures 210 present a loop-like channel for insertion of the quick release bar 130 therethrough. The hangers 200 support the release bar 130 and are used with the lower arch bar 120 and ligature wires 500, 600 in a manner to provide a quick release system as above described.

FIG. 7 shows another embodiment of a hanger 220 which is clamped about a flat arch bar 222. Each hanger 220 comprises a tab 224 folded about the upper edge 223 of the arch bar 222. A pair of depending support loops 226 and 228 are connected to tab 224 for insertion of the release bar 130 therethrough. A plurality of such hangers 220 may be selectably placed along the arch bar. As such the arch bar 222 with hangers 220 thereon may be used in place of bar 102 in system 100.

As shown in FIG. 7, the loops 226, 228 include a depending portion connected to the tab 224 at the upper end of the tab, and an upturned portion connected to the bottom end of the depending portion. When the release bar is extended through the loops 226, 228 of each hanger 220, the upturned loop portions space the release bar from the flat arch bar.

An alternative hanger 240 is shown in FIG. 11 for attachment to a flat 222 arch bar. Hanger 240 presents a loop 242 through which the arch bar 222 is inserted. The hanger 240 presents a pair of depending loops 246 and 248 through which a portion of the release bar 130 is extended. A plurality of such hangers 240 are longitudinally spaced along the extent of the arch bar 222 according to the desires of the treating practitioner. Arch bar 222 with hangers 240 thereon may be used in place of arch bar 102 in system 100.

As shown in FIG. 11, the loops 246, 248 include a depending portion connected to the tab 242 at the upper end of the tab, and an upturned portion connected to the bottom end of the depending portion. When the release bar is extended through the loops 246, 248 of the hanger 240, the upturned loop portions space the release bar from the flat arch bar.

FIGS. 8 and 9 show a grip 134 tied 611 to the handle 133 of the quick release bar 130. Accordingly, such grip 134 allows for easier purchase of the handle by the user.

FIG. 10 is a sectional view of a cap 700, on an enlarged scale, showing an internal bore 710 and a smaller bore 712 extending therefrom. One end of wire 500b is passed through bore 712 and out the bore 710. During wiring the adjacent end of wire 500a is wound about end of 500b to produce a twisted end 510. The cap is then slidable over twist 510 so as to place twist 510 within the bore 710. Accordingly, the cap 700 precludes the twist 510 from rubbing against the adjacent oral tissue. Also, the cap 700 precludes the need to use wax on the twist 510 which in turn reduces the oral debris.

FIG. 13 shows a sectional view of an alternative cap 700' similar to cap 700. Cap 700' includes an additional bore 714 extending from the internal bore/housing 710. In utilizing cap 700' the ends of wire 500a, 500b both pass through the second bore 714 and are twisted exterior of the cap 700'. The portion of the twisted end extending beyond the cap 700' is then cut off. The remaining twist is within bore 714. The cap may be slid along the twist to assure that the free end of the twist lies within the bore 714. Cap 700' may be utilized in lieu of cap 700. It is understood that both caps may also be used in connection with the twisted ends 610 of the ligature wires 600.

FIG. 12 illustrates a quick release bar holder 140. The holder 140 presents an elongated sleeve 141 which is inserted through the plurality of loops or orifices of the various arch bars, e.g. 160 as above described. A flange 144 at the distal end 143 of the holder 140 presents notches 142 which engage a distal loop 164' extending from the arch bar 160 so as to maintain the holder 140 in place. Upon placement of the holder in the arch bar the sleeve 141 is cut approximately at position 145. The distal end of a quick release bar 130 is inserted through loops 164 and into the soft material presented by the remaining flange 144. The flange 144 maintains the bar 130 in place and precludes the bar from abrading adjacent tissues. Once holder 140 and release bar 130 therein are in place the tie wires 600 are wrapped about the bar 130 as above described. The holder 140 may also be used with the above-described hangers 200. As such the sleeve 141 is inserted through the apertures 210 found in support legs 206, 208. The notches 142 engage one of the support legs. The portion of sleeve 141 extending beyond the other of the support legs 206 or 208 is then cut off presenting an aperture. The end of release bar 130 is then inserted through the aperture 210 in each leg 206, 208 and into the aperture of the engaged flange of the holder 140. This structure is used with a hanger 200 attached to a distal tooth of a dental arch.

It is to be understood that while certain forms of this invention have been illustrated and described, it is not limited thereto except insofar as such limitations are included in the following claims and allowable functional equivalents thereof.

What is claimed:

1. An apparatus for use in holding together the upper and lower dental arches of a patient, comprising:
   a first arch bar formed of an elongated flat band of malleable material capable of being conformed to the curvature of the dental arches of the patient, the band presenting opposing front and back surfaces and upper and lower edges and defining a longitudinal axis;
   a plurality of closed loops supported on the first arch bar and protruding from the front surface of the flat band, each loop presenting an opening extending in a direction parallel to the longitudinal axis of the first arch bar, and the loops being spaced from one another along the longitudinal axis to define a channel;
   a second arch bar formed of a malleable material capable of being conformed to the curvature of the dental arches of the patient;
   a fastening means for fastening the first and second arch bars to the dental arches of the patient;
   an elongated release bar formed of a malleable material capable of being conformed to the curvature of the longitudinal axis of the first arch bar and presenting proximal and distal ends, the release bar being sized for receipt in the channel defined by the loops and including a means at the proximal end for permitting gripping and handling of the release bar; and
   a tying means for tying the release bar and the second arch bar together when the release bar is received in the channel to immobilize the arch bars relative to one another, the release bar being removable from the channel to release the tying means so that the first and second arch bars are movable relative to one another.

2. An apparatus as recited in claim 1, wherein the lower edge of the flat band extends above the loops so that when the release bar is received in the channel it is spaced beneath the flat band of the first arch bar to facilitate application of the tying means.

3. An apparatus as recited in claim 1, wherein each loop includes a spacing means for spacing the release bar from the flat band when the release bar is received in the channel, facilitating placement of the tying means.

4. An apparatus for use in holding together the upper and lower dental arches of a patient, comprising:
   a first arch bar formed of an elongated flat band of malleable material capable of being conformed to the curvature of the dental arches of the patient, the band presenting opposing front and back surfaces and upper and lower edges and defining a longitudinal axis;

a plurality of closed loops supported on the first arch bar and protruding from the front surface of the flat band, each loop presenting an opening extending in a direction parallel to the longitudinal axis of the first arch bar, and the loops being spaced from one another along the longitudinal axis to define a channel;

a second arch bar formed of a malleable material capable of being conformed to the curvature of the dental arches of the patient;

a fastening means for fastening the first and second arch bars to the dental arches of the patient;

an elongated release bar formed of a malleable material capable of being conformed to the curvature of the longitudinal axis of the first arch bar and presenting proximal and distal ends, the release bar being sized for receipt in the channel defined by the loops and including a means at the proximal end for permitting gripping and handling of the release bar; and a tying means for tying the release bar and the second arch bar together when the release bar is received in the channel to immobilize the arch bars relative to one another, the release bar being removable from the channel to release the tying means so that the first and second arch bars are movable relative to one another, wherein each loop includes a depending portion supported on the upper edge of the flat band and an upturned portion that is turned inward toward the front surface of the band and upward to form the loop, the upturned portion defining a spacing means for spacing the release bar from the flat band when the release bar is received in the channel, facilitating tying of the tying means.

5. An apparatus for use in holding together the upper and lower dental arches of a patient, comprising:

a first arch bar formed of an elongated flat band of malleable material capable of being conformed to the curvature of the dental arches of the patient, the band presenting opposing front and back surfaces and upper and lower edges and defining a longitudinal axis;

a plurality of closed loops supported on the first arch bar and protruding from the front surface of the flat band, each loop presenting an opening extending in a direction parallel to the longitudinal axis of the first arch bar, and the loops being spaced from one another along the longitudinal axis to define a channel;

a second arch bar formed of a malleable material capable of being conformed to the curvature of the dental arches of the patient;

a fastening means for fastening the first and second arch bars to the dental arches of the patient;

an elongated release bar formed of a malleable material capable of being conformed to the curvature of the longitudinal axis of the first arch bar and presenting proximal and distal ends, the release bar being sized for receipt in the channel defined by the loops and including a means at the proximal end for permitting gripping and handling of the release bar;

a housing for the distal end of said release bar, said housing including a sleeve for insertion through at least one of said loops, means for engaging said sleeve to said first arch bar and an aperture for insertion of said distal end of said release bar into said sleeve; and a tying means for tying the release bar and the second arch bar together when the release bar is received in the channel to immobilize the arch bars relative to one another, the release bar being removable from the channel to release the tying means so that the first and second arch bars are movable relative to one another.

6. The apparatus as claimed in claim 5 wherein said engaging means comprises:

a flange at an end of said sleeve and containing said aperture;

a notch in said flange for engaging one of said plurality of loops after insertion of said sleeve through said loop.

7. An orthodontic surgery apparatus for use in holding together the upper and lower dental arches of a patient comprising:

a first arch bar for the upper dental arch;

channel means on said arch bar for presenting a channel projecting from said first arch bar for insertion of a release bar therethrough;

an elongated tab attached to said channel means, the tab being folded about said first arch bar to connect said channel means to said first arch bar;

a second arch bar for the lower dental arch;

a release bar having proximal and distal ends for extension through said channel means of said first arch bar; and means extending between said release bar and said second arch bar in a manner for urging said first arch bar and said second arch bar, and said dental arches together;

said proximal end of said release bar being manipulated by a user to withdraw said release bar from said channel means and said urging means, whereby to allow said first and second arch bars and dental arches to move in a direction apart from each other.

8. An arch bar for use in an apparatus for holding together the upper and lower dental arches of a patient, the arch bar comprising:

an elongated flat band of malleable material capable of being conformed to the curvature of the dental arches of the patient, the band presenting opposing front and back surfaces and upper and lower edges and defining a longitudinal axis, a plurality of closed loops that are spaced from one another along the longitudinal axis and protrude from the front surface and lower edge of the flat band, each loop being secured to the band with the loop presenting an opening extending in a direction parallel to the longitudinal axis, and including an upper end secured to the band and a lower end that is turned inward toward the band.

9. An arch bar as recited in claim 8, wherein the lower end of the loop includes an upturned free end that extends above the lower edge of the band.

10. An arch bar as recited in claim 8, wherein the upper end of the loop is secured to the upper edge of the band, and the lower end of the loop includes an upturned free end that terminates at the upper end to form the loop.

* * * * *